United States Patent [19]
Fuchs

[11] Patent Number: 5,427,280
[45] Date of Patent: Jun. 27, 1995

[54] MEDIA DISPENSER WITH DOSING STROKE LIMITER

[75] Inventor: Karl-Heinz Fuchs, Radolfzell, Germany

[73] Assignee: Ing. Erich Pfeiffer GmbH & Co. KG, Germany

[21] Appl. No.: 930,418

[22] PCT Filed: Mar. 12, 1991

[86] PCT No.: PCT/EP91/00457
§ 371 Date: Nov. 16, 1992
§ 102(e) Date: Nov. 16, 1992

[87] PCT Pub. No.: WO91/13689
PCT Pub. Date: Sep. 19, 1991

[30] Foreign Application Priority Data
Mar. 14, 1990 [DE] Germany .............. 40 08 068.4

[51] Int. Cl.⁶ .................................. B65D 88/54
[52] U.S. Cl. .................... 222/320; 222/386
[58] Field of Search .......... 222/162, 309, 319–321, 222/183, 153, 327, 340, 325, 326, 386; 604/214, 218, 227, 234

[56] References Cited

U.S. PATENT DOCUMENTS

| | | | |
|---|---|---|---|
| 1,926,367 | 9/1933 | Booth | 222/320 |
| 3,128,916 | 4/1964 | Picot | 222/183 |
| 3,279,654 | 10/1966 | Pierick | 222/386 |
| 4,017,007 | 4/1977 | Riccio | 222/325 |
| 4,061,254 | 12/1977 | Nilson | 222/494 |
| 4,074,831 | 2/1978 | Roach | 222/309 |
| 4,175,704 | 11/1979 | Cohen | 222/320 |
| 4,433,799 | 2/1984 | Corsette | 222/309 |
| 4,612,010 | 9/1986 | Hamacher et al. | 222/340 |
| 4,871,092 | 10/1989 | Maerte | 222/309 |
| 4,921,142 | 5/1990 | Graf et al. | 222/386 |
| 4,946,069 | 8/1990 | Fuchs | 222/321 |
| 4,962,868 | 10/1990 | Borchard | 222/309 |
| 5,257,726 | 11/1993 | Graf et al. | 222/386 |

FOREIGN PATENT DOCUMENTS

| | | |
|---|---|---|
| 0088928 | 9/1983 | European Pat. Off. |
| 0098373 | 1/1984 | European Pat. Off. |
| 0098939 | 4/1984 | European Pat. Off. |
| 0311863 | 8/1989 | European Pat. Off. |
| 2242113 | 3/1975 | France . |
| 2300916 | 9/1976 | France . |
| 2143471 | 3/1973 | Germany . |
| 2536473 | 2/1977 | Germany . |
| 2702539 | 8/1977 | Germany . |
| 3311747 | 10/1983 | Germany . |
| 3631341 | 4/1987 | Germany . |

Primary Examiner—Andres Kashnikow
Assistant Examiner—Philippe Derakshani
Attorney, Agent, or Firm—Quarles & Brady

[57] ABSTRACT

In an applicator for single use without pump suction, a plurality of partial strokes can be executed sequentially and releasably limited at the corresponding end by a limited stop. The stopping device provided for this purpose is arranged between two cap-shaped housing parts which interlock at their open ends. The housing parts fully accommodate a pump and are connected to each other by a snap connection.

29 Claims, 2 Drawing Sheets

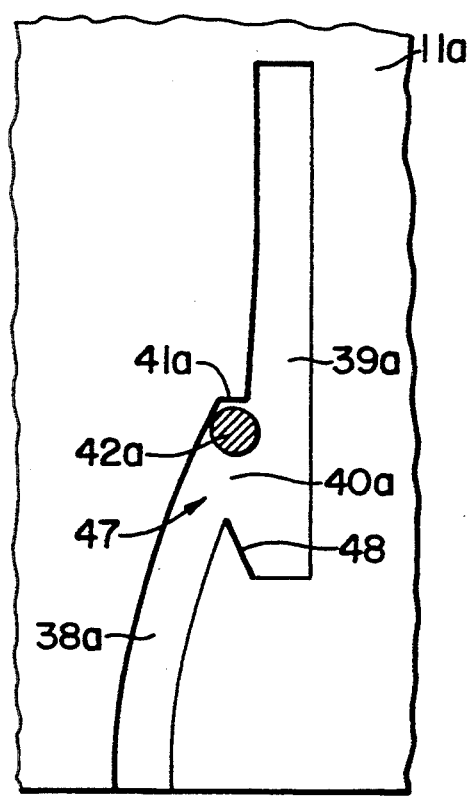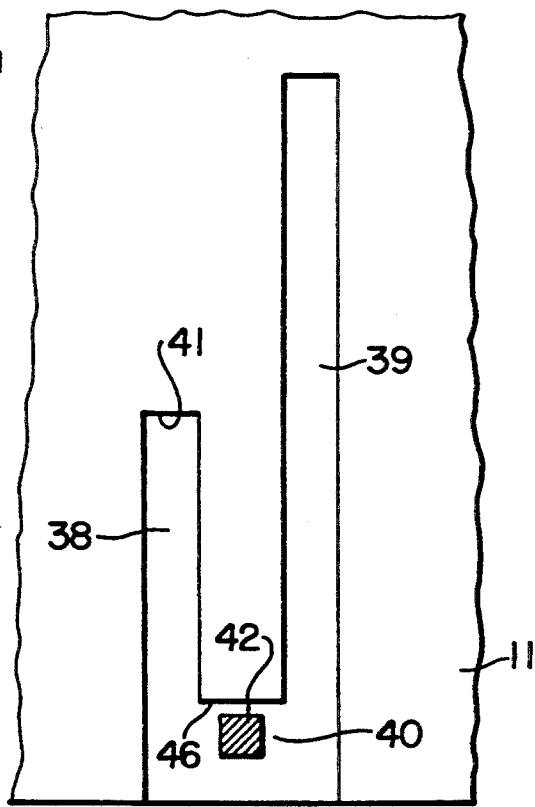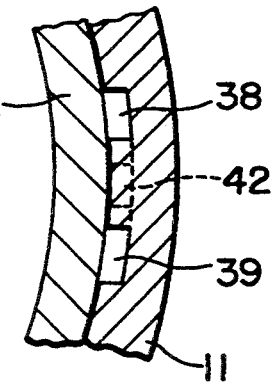

MEDIA DISPENSER WITH DOSING STROKE LIMITER

FIELD OF THE INVENTION

The invention relates to a discharge apparatus for flowable media, which can be gaseous or slightly volatile, liquid or pasty, pulverulent or the like. According to the invention, it can have at least one manually operable pump and a discharge opening connected to its pump chamber by means of an outlet channel, such as an atomizing nozzle, so that by manual operation an easy discharge of at least one predetermined medium quantity is ensured.

BACKGROUND OF THE INVENTION

The invention is based on the problem of avoiding the disadvantages of known solutions and in particular providing a manually operable discharge apparatus with which, in directly succeeding manner, two or more predetermined medium quantities can be discharged, preferably through the same discharge opening and by operating the same handles.

SUMMARY OF THE INVENTION

According to the invention means are provided in order to so limit at least one partial stroke at its stroke end that it is possible to switch to a further extending partial stroke. The preferably outwardly tightly sealed, inlet-free pump chamber stores the entire medium quantity to be discharged and is emptied in the partial strokes without refilling.

For limiting stroke to a partial stroke, it is possible to provide an arresting device with stops for the components that are slidable against one another. In addition, one of these components can, at the end of its partial stroke and before reaching the pump stroke end position, assume a position with respect to the other component such that, without engaging around, it could not, or could only be very difficulty, further operated to the end position. If the handle of the first-mentioned component is formed by the cross-member of a clip or the end wall of a cap, then the latter can be operated by a thumb positioned roughly radially thereto until it terminates roughly flush with an associated casing end of the other component. For a further actuation or stroke, in which the handle of one component is completely flush in the other, it is necessary to engage the thumb into one of the components that it is positioned roughly axially to the actuation direction.

The arresting means or device is appropriately provided between two casing parts, whereof at least one is the lowerable, substantially dimensionally stable part. This part preferably forms a substantially completely closed outer casing for the complete discharge apparatus, or at least the pump. A connection piece-like or similar discharge extension which has the discharge opening for the apparatus alone optionally projects from this casing. The layer of the two casing parts is appropriately connected or substantially in one piece with the discharge extension piece.

The arresting means can be provided in space-saving, easily fittable manner in the vicinity of a lower end of the discharge apparatus, such as in the discharge position behind the pump chamber end facing the discharge opening. Furthermore, for passing from one partial stroke to the next, it is possible to provide a changeover or sequence control, e.g. in the manner of a changeover of a multicolored writing implement operable by means of a single pushbutton, so that the pump is not returned to the starting position between two partial stokes. If it is returned to said starting position, then it can be advantageously used for sucking empty the outlet channel and optionally for sucking air into the pump chamber. However, it is also conceivable, despite the return of the components or the handles into the starting position, to prevent a return of the pump into the starting position by the provision of a type of freewheel.

The pump is preferably constructed as a thrust piston pump with a simple, dimensionally stable storage or cylindrical container, whose jacket is in one piece with its bottom. If the cylindrical container is inserted in stop-limited manner in a sliding guide of one component whose friction compared with the container is similar than that of the pump piston or a component connected thereto, the pump cylinder substantially stops with respect to the pump piston at the end of each partial stroke, whereas the component with the associated handle and having the sliding guide is returned towards the starting position.

The pump which is located completely and with radial spacing within the outer casing and whose pump piston and cylinder can be positioned in any position between the end walls of said outer casing, can also be protected within an inner cage or casing radially spaced within the outer casing and which optionally extends substantially over the entire length thereof. This inner casing, like the outer casing, can comprise two caps telescopically interengaging with their open sides and engage in one another in stop-limited manner in the starting position. The cap optionally form a guide for a return or restoring spring located within a circular space. The caps are interconnected by a snap connection or the like, which forms the sole axial means preventing accidental release of the two components with respect to one another following assembly.

BRIEF DESCRIPTION OF THE DRAWINGS

These and further features of preferred developments of the invention can be gathered from the claims, description and drawings and the individual features, either singly or in the form of subcombinations, can be realized in an embodiment of the invention and in other fields and can represent advantageous, independently protectable constructions, for which protection is hereby claimed. The invention is described in greater detail hereinafter relative to embodiments and the attached drawings, wherein show:

FIG. 2 A detail of FIG. 1 in elevation.

FIG. 3 The detail of FIG. 2 in cross-section.

FIG. 4 Another embodiment in a representation corresponding to FIG. 2.

DETAILED DESCRIPTION OF THE PREFERRED EMBODIMENTS

Figure 1:
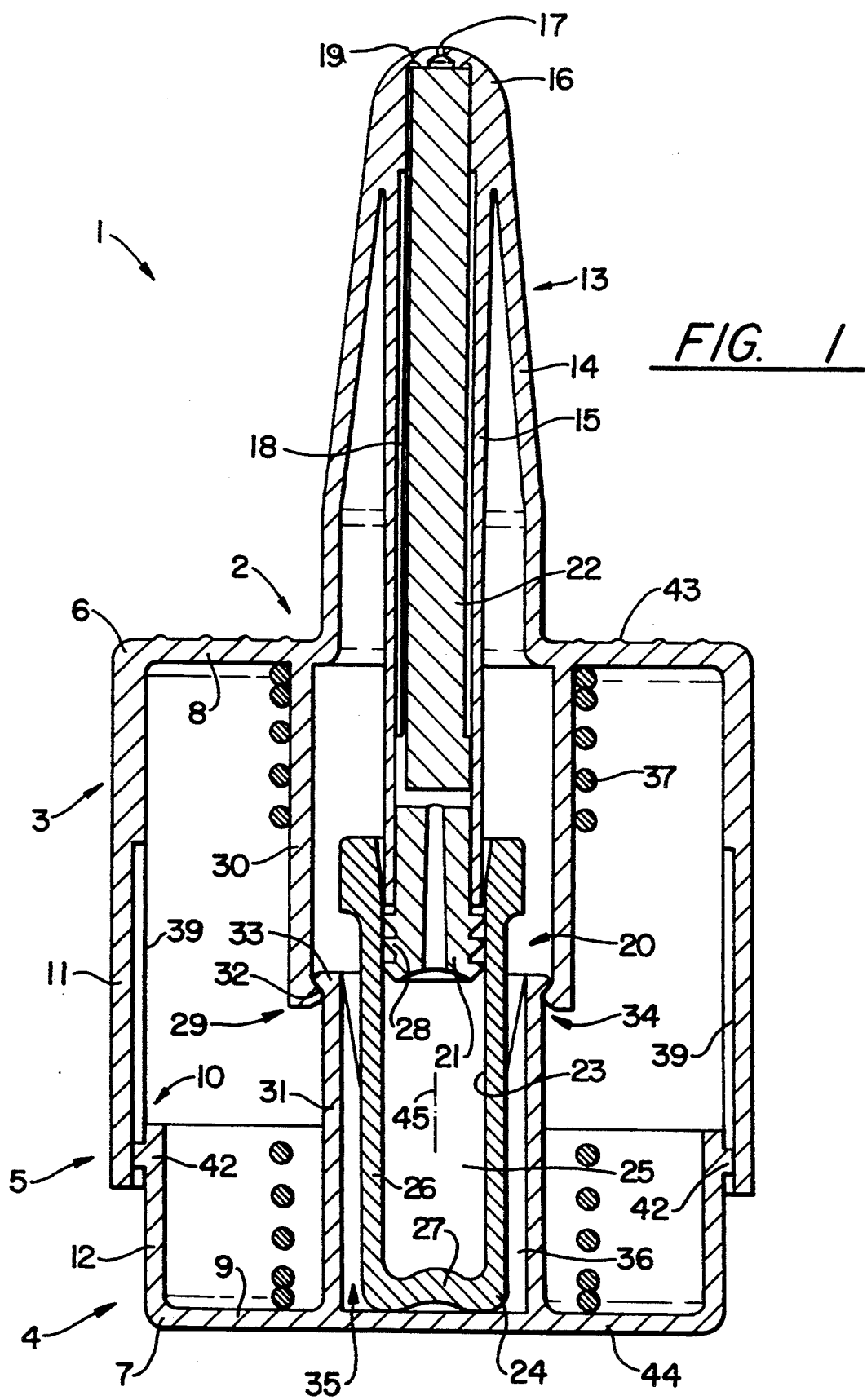
FIG. 1 An inventive discharge apparatus in axial section.

The discharge apparatus 1 has a substantially one-piece basic body 2, which forms one of two components, 3, 4 axially displaceable against one another. Together, these two components form a substantially slightly stepped, cylindrical outer casing 5, whose length is roughly the same as its diameter of e.g. only approximately 30 mm. The thin-walled casing 5 is bounded and defined by two cap-like casing parts 6, 7, whereof that of the basic body 2 closely surrounds at the outer circumference the other casing part 7. Each casing part 6 or 7 has an approximately planar end wall 8 or 9 and an approximately cylindrical jacket 11 or 12. With the jackets 11, 12 is associated an arresting means 10, which as a function of the rotary position of the parts 6, 7 relative to each other, differently directly limits in different names the stroke of the two casing parts 6, 7 against one another.

A significantly reduced diameter extension piece 13 projects in the center from the outside of the end wall 8 of the casing part 6 and is essentially formed by an outer sleeve 14 whereof one end transition in one piece to the end wall 8 and an inner tube 15 which is radially spaced from the sleeve 14. At their front ends the sleeve 14 and the tube 15 pass into one another in one-piece for forming a nozzle cap 16. In the end wall of the nozzle cap 16 is provided a discharge opening 17 leading into the open and which, accompanied by the interopposing of a twisting device 19, is connected to one end of an outlet channel media duct 18.

Within the outer casing 5 is positioned a pump 20. A one-piece pump piston 21 with piston shaft 22 and cylinder 23, which is formed by an almost completely closed, medium-filled container 24, form the pump 20. Apart from the storage area, the interior also forms the pump chamber 25 which is exclusively tightly closed at one end by the pump piston 21. The container 24 is formed by a substantially cylindrical jacket 26 and a bottom 27, whose piston path is open to its full width at the open end which is provided with a projecting outer edge or is widened in funnel-shaped manner, without providing a cylinder cover or the like.

At its end that is remote from the pump piston 21, the piston shaft 22 forms a component of the twisting device 19 and an end boundary of the inner end of the outlet opening 17. The outlet channel 18 connects to the pump chamber 25 within the pump piston 21 and then passes as a transverse channel into a portion positioned between the outer circumference of the piston shaft 22 and the inner circumference of the inner sleeve 15. The piston shaft 22 has two stepped, outside diameter-decreasing shaft portions towards the outlet opening 17. One is located on the pump piston 21 being closely positioned in the bore of the inner sleeve 15, which is correspondingly stepped spaced from said portion close to the associated shaft end, so that it closely embraces the latter, but between the same has a limited gap spacing from the outer circumference of the piston shaft 22. The pump piston 21 has several, e.g. three directly adjacent, succeeding, approximately acute-angled or saw-tooth flanked piston lips 28 separated from one another by corresponding acute-angled ring grooves and constructed in one piece therewith, whose sloping flanks forms in each case their front flanks and which engage with pretension on the inner circumference of the cylinder 23. The inner sleeve 15, which passes in contact-free manner the end wall 8 and freely projects into the outer casing 5 can extend in the cylinder 23 to close to the rear end of the pump piston 25 and can slide on the inner circumference of the cylinder 23.

A smaller, but roughly equally long, cylindrically stepped inner casing 29 is spaced within the casing 5, which substantially comprises an outer sleeve 30 and an inner sleeve 31 which serves as a reception member. The outer sleeve 30, which is only slightly wider than the outer sleeve 14, projects in one piece from the inside of the end wall 8 less far than the jacket 11 and is open throughout to the inner area of the outer sleeve 14. The jacket of the inner sleeve 31 is correspondingly connected in one piece directly to the inside of the end wall 9 and projects axially further than the jacket 12 and therefore beyond its end face. At their free ends, the sleeves 30, 31 have in each case a collar-like stop 32 and 33 for reciprocal engagement purposes in such a way that the component 4 cannot be removed axially from the outer component 3 in the pump stroke starting position shown in FIG. 1. Simultaneously, these stops form a self-widening snap connection 34 for the spring detent-like connection of the two components 3, 4 on assembly. The end of the pump piston 21 is slightly set back relative to the end face of the outer sleeve 30.

The inner sleeve 31 forms a sliding or plug-in receptacle 35 or reception member for the container 24, which projects past the inner end faces of the jacket 12 and the inner sleeve 31 and which in the assembly position is engaged in supporting manner on the bottom of the inner sleeve 31 or on the inside of the end wall 9 and which is otherwise only secured on its outer circumference. To this end, the container 24 does not rest on the inner circumference of the inner sleeve 31, but on uniformly circumferentially distributed radial ribs 36 or on their radially inner edge faces. If said engagement is provided with pretension, then the container 24 performs all the movements together with the component 4. However, the engagement can also form a sliding guide, so that the container 24 always maintains the position which it has reached relative to the pump piston 21 in the manner of a delayed-action clutch or coupling during return movements of the component 4.

It is also conceivable to construct the container 24 in substantially free-standing, one-piece manner with the component 4 and to do away with the inner casing 29. In the pump stroke end position, the open end of the container 24 projecting past the inner sleeve 31 is almost entirely located within the outer sleeve 14, in which its outer edge can be secured to prevent withdrawal. The end face of the inner sleeve 31 has a limited gap spacing from the inner face of the end wall 8 and the bottom wall 9 with a corresponding gap spacing from the end face of the outer sleeve 30. Thus, it is ensured that the inner face of the pump piston 21 can be moved up to the bottom 27 of the container 24 and the pump movement is stop-limited by this only.

The arresting or stop control means 10 has several, e.g. two cams 42 uniformly distributed around the circumference of the part 7, which project past outer circumference. With each cam 42 is associated a number of directly adjacent longitudinal guides 38, 39 corresponding to the number of partial strokes. The guides are formed by grooves in the inner circumference of the jacket 11 and emanate from its open end face and only extend over part of its length. The end face 41 of the shorter longitudinal guide 39 forms a stop for the cam 42 at the end of the first partial stroke, after which approximately half of the stored quantity of approximately 0.1 ml has been discharged from the container 24. At the end of this partial stroke the outside of the end wall 9 of the casing part 7 is approximately in one plane with the associated end face of the casing part 6. Adjacent to the starting end at said end face, the longitudinal guides 38, 39 are interconnected by means of a transverse guide 40.

At the end of the first partial stroke, the component 4 is returned to the starting position with the cam 42 by a return spring 37, which is located in the annular space between the two casings and supported on the end walls 8, 9. By turning the component 4 relative to the component 3, the cam 42 can be brought through the transverse guide 40 the starting end of the longitudinal guide 39. The cam 42 strikes against the associated flank of the longitudinal guide 39, because the corresponding flanks of the longitudinal guides 38, 39 at both sides are located at the ends of the transverse guide 40. Now, in a further stroke, the remainder can be pumped out of the container 24 and the cam 42 appropriately does not have to strike against the end face of the longitudinal guide 39. From this end position, the casing part 7 can again return to its starting position.

The outside of the end wall 8 forms a pressure handle 43 that surrounds in circular manner the extension piece 13, while the outside of the end wall 9 forms a pressure handle 44, whose external diameter is approximately the same as that of the handle 43. The discharge apparatus 1 is generally operated with three fingers, the index and middle finger engaging on the handle 43. Substantially all the components and constructions are aligned along a common central axis 45 or are symmetrical thereto.

The component 4 can be releasably arrested against pump movements in the starting position. For example, the associated transverse boundaries of the transverse guide 40 located between the longitudinal guides 38, 39 can form a stop face 46 for the cam 42, so that prior to putting into use the cam 42 must be rotated. The cams 42 could also be provided for producing the snap connection between the two components 3, 4 or for their axial release prevention in the starting position. In this case the longitudinal guides 38, 39 and optionally the transverse guide 40 would be closed at their associated ends located at the end face of the jacket 11.

It would also be possible to completely obviate the need for a return spring 37. For example, according to FIG. 4, the transverse guide 40a could be next to the end face 41a of the longitudinal face 38a, so that the cam 42a could be rotated directly into the following longitudinal guide 39a without an axial return movement. Particularly, if in this case, a return spring 37 is provided, through a small, axial return movement, it is possible to ensure that under the tension of said spring the cam 42a runs up onto an included control flank 48 and therefore, in self-oriented manner, is transferred to the start of the longitudinal guide 39a, which give a sequence control 47.

As a result of the reciprocal position of the components 3, 4, it is possible to establish how many partial strokes have been performed, which in simple manner, provides an indicator.

Together with the container 24, the component 4 forms an assembly unit, which in a single plugging process can be connected to the outer assembly unit formed from the component 3 and the pump piston 21. As a result, the discharge apparatus 1 can be very easily filled and assembled or closed.

I claim:

1. A dispenser (1) for discharging media, comprising:
   a base body (2);
   a reception member (31) providing a container reception (35) for receiving a separate media container (24), said reception member (31) being operationally displaceable with respect to said base body (2) in an operating motion from an initial position over an actuating path to an ultimate end position;
   a media duct (18) at least partly traversing said base body (2); and
   at least one casing (5, 29) for substantially entirely enclosing the container (24) when positioned in said container reception (35), said reception member (31) providing a section of said at least one casing (5, 29) having at least one end wall (8, 9), said container reception (35) being made in one part with said end wall (9), wherein one of said at least one casing (5) is an external casing (5) of said dispenser (1), said external casing (5) having an external casing member (6), said external casing member (6) being cup-shaped and having a freely projecting external casing jacket (11), said base body (2) providing said casing member (6), said reception member (31) being provided with a spacing from said casing jacket (11) within said casing jacket (11).

2. The dispenser according to claim 1, wherein said at least one casing (5) provides step control means (10) for positively limiting said actuating path to partial path sections, thereby providing at least one intermediate position between said initial position and said ultimate end position, and further providing operationally limited states of said dispenser (1).

3. The dispenser according to claim 2, wherein said operating motion is a thrust motion releasably limitable with said step control means (10) in at least one of:
   said initial position and
   said intermediate position, thereby providing said operationally limited states of said dispenser (1).

4. The dispenser according to claim 3, wherein said step control means (10) is provided for stop limiting said operating motion, in at least one of:
   said initial position and
   said intermediate position at least one of said limited state being releasable by a rotary motion.

5. The dispenser according to claim 2, wherein at least one of said limited states is releasable without a return motion of said container reception (34), said step control means (10) providing displaceably interengaging first and second control members (41, 42), said first control member (41) being provided by an end face of a longitudinal guide (38) slidingly receiving said second control member (42).

6. The dispenser according to claim 2, wherein for freeing said dispenser (1) from one of said limited states to permit motion on a further path section, said limited state is releasable with a return motion of said container reception (35), release control means (48) being provided for effecting a release motion of said step control means (10) as a function of said return motion.

7. The dispenser according to claim 1, wherein return spring means (37) are provided for counteracting said operating motion.

8. The dispenser according to claim 2, wherein said casing (5) provides said casing jacket and second, third and fourth casing jackets operationally reciprocally telescoping, said step control means (10) providing displaceably interengaging first and second guide members, said guide members being provided on said casing jackets.

9. The dispenser according to claim 1, wherein said external casing (5) of said dispenser (1) has a second casing member (7), said second casing member (7) being operationally displaceable with respect to said casing member (6), said reception member (31) being provided with a spacing from said external casing within said external casing (5).

10. A dispenser for discharging media, comprising:

a base body (2) providing an external casing (5) including a casing member (6) of said dispenser (1), said casing member (6) being cup-shaped;

a second casing member (7) being provided and being operationally displaceable with respect to said first casing member (6), said second casing member (7) providing a container reception (35) for receiving a media container (24) having a media chamber (25), and a media duct (18) at least partly provided in said base body (2) and provided for transferring the media out of the media chamber (25) after the media container (24) is positioned in said container reception (35); and an inner cage (29) at least partly within said external casing (5), said inner cage (29) providing said container reception (35) and being at least partly provided by said second casing member (7).

11. The dispenser according to claim 10, wherein said inner cage (29) provides a reception member (31) separate from said base body (2), said reception member (31) providing said container reception (35).

12. The dispenser according to claim 10, wherein said inner cage (29) has a radial spacing from said external casing (5), said inner cage (29) defining a length extension, said external casing (5) extending substantially entirely over said length extension.

13. The dispenser according to claim 10, wherein said inner cage (29) provides two cage members (30, 31) including a mounting member (30) and a reception member (31) operationally displaceably with respect to each other, said reception member (31) providing said container reception (35) and displaceably engaging said mounting member (30).

14. The dispenser according to claim 13, wherein said casing member (6) has a member jacket (11) and an end wall (8) providing a wall inside and a wall outside, said member jacket (11) and said mounting member (30) projecting from said wall inside and providing a free member end (32), said reception member (31) telescopingly engaging said mounting member (30), said mounting member (30) projecting less far than said member jacket (11), said wall outside providing at least one operating handle (43).

15. The dispenser according to claim 13, wherein at least one snap connection (34, 40) is provided for reciprocally securing said cage members (30, 31) against reciprocal displacement in at least one of two opposing motion directions.

16. The dispenser according to claim 13, wherein at least one snap connection (34) is provided, said cage members (30, 31) interengaging by said snap connection (34) provided in the vicinity of at least one free end (32, 33) of at least one of said cage members (30, 31), said snap connection (34) being provided to prevent withdrawal of said reception member (31) from said mounting member (30).

17. The dispenser according to claim 10, wherein said dispenser (1) defines an initial state, locking means (40, 41) being provided for locking said dispenser (10) against actuation in said initial state, said locking means being releasable by manual actuation.

18. The dispenser according to claim 13, wherein said container reception (35) has a free member end (33) and is provided to receive the media container (24) in an operating state, in said operating state the media container (24) freely projecting over said free member end (33), said container reception (35) engaging inside said mounting member (30) and having a bottom wall (9) providing a bottom inside, said bottom inside providing a support for a container bottom (27) of the media container (24) when positioned in said container reception (35).

19. The dispenser according to claim 10, wherein said container reception (35) provides rib members (36) for supportingly engaging the media container (24) when positioned in said container reception (35).

20. The dispenser according to claim 10, wherein said container reception (35) provides a slide reception for the media container (24) when positioned in said container reception (35), said container reception (35) being provided in a reception member (31) separate from said base body (2), said reception member (31) being at least one of:
bow-shaped in cross-section and
cup-shaped.

21. The dispenser according to claim 10, wherein said container reception (35) is provided in a reception member (31), when positioned in said container reception (35), the container (24) and said reception member (31) commonly providing a mounting assembly to be mounted on said base body (2).

22. The dispenser according to claim 10, wherein said casing member (6) has an end wall (8) providing a wall inside and a wall outside, said wall outside defining a wall width extension, a discharge stud (13) being provided and projecting from said wall outside, said discharge stud (13) defining a stud width extension substantially smaller than said wall width extension, said discharge stud (13) having an external jacket (14) dimensioned to operationally receive the media container (24) when positioned in said container reception (35), said discharge stud (13) boarding said media duct (18).

23. The dispenser according to claim 10, wherein said container reception (35) is provided by a reception member (31), said reception member (31) providing an external casing element (7) of said external casing (5), said external casing element (7) telescopingly engaging said casing member (6).

24. The dispenser according to claim 10, wherein a thrust piston pump (20) including a pump piston (21) is provided, said pump piston (21) being displaceable commonly with said base body (2), said pump piston (21) being provided to slide in the container (24) when positioned in said container reception (35).

25. A dispenser for discharging media, comprising:
a base body (2);
a reception member (31) providing a container reception (35) for receiving a media container (24), said reception member (31) being operationally displaceable with respect to said base body (2) from an initial position (46) to operating positions including at least one end position (38, 39) over an actuating path; and holding means (14, 21) for positionally holding the container (24) with respect to said base body (2) after the container (24) is positioned in said container reception (35) and when said reception member (31) is returned from at least one of said operating positions (38, 39) towards said initial position in a return motion.

26. The dispenser according to claim 25, wherein said container reception (35) is a slide reception for slidingly receiving the container (24) when positioned in said container reception (35), said base body (2) providing said holding means (14, 21) for holding the container (24) in at least one of said operating positions against said return motion, the container (24) sliding in said container reception (35) when the container (24) is positioned in said reception member (31) and when said reception member (31) performs said return motion.

27. The dispenser according to claim 25, wherein said holding means (14, 21) is a clamping means for clampingly engaging the container (24) after said container is positioned into said container reception (35).

28. The dispenser according to claim 25, wherein said dispenser (1) provides a discharge stud (13) defining a stud inside, said stud inside providing said holding means (14).

29. The dispenser according to claim 25, wherein a displacement member (21) is provided for engaging inside the container (24) when mounted in said container reception (35), said displacement member (21) providing said holding means (28).

* * * * *